US008272389B2

(12) United States Patent
Bish (10) Patent No.: US 8,272,389 B2
(45) Date of Patent: Sep. 25, 2012

(54) COMPACT MIRROR FLOSS CONTAINER (76) Inventor: Charity L. Bish, Provo, UT (US)

( * ) Notice: Subject to any disclaimer, the term of this patent is extended or adjusted under 35 U.S.C. 154(b) by 826 days.

(21) Appl. No.: 12/027,569

(22) Filed: Feb. 7, 2008

(65) Prior Publication Data

US 2009/0199865 A1     Aug. 13, 2009

(51) Int. Cl.
*A61C 15/00* (2006.01)
*B65D 71/00* (2006.01)
*B65D 85/00* (2006.01)
*A61B 19/02* (2006.01)
*A45D 42/00* (2006.01)

(52) U.S. Cl. ....... 132/325; 132/316; 206/581; 206/63.5; 206/389

(58) Field of Classification Search ........... 132/325, 132/323, 324, 328, 296, 301, 304, 309, 316, 132/293, 291, 295, 299, 305, 315, 329; D28/64, D28/65, 67, 68, 64.1, 64.3; 206/581, 823, 206/63.5, 389, 233, 238, 235; 220/324, 326; 225/43, 45, 46
See application file for complete search history.

(56) References Cited

U.S. PATENT DOCUMENTS

| | | | | |
|---|---|---|---|---|
| 1,853,453 | A | * | 4/1932 | Priest .............................. 132/309 |
| D211,880 | S | * | 8/1968 | Di Giuseppe ................... D28/66 |
| 3,871,393 | A | * | 3/1975 | Wharton ........................ 132/326 |
| 4,254,786 | A | | 3/1981 | Won |
| D271,431 | S | | 11/1983 | Seelig |
| 4,412,821 | A | | 11/1983 | Sturdivant |
| 4,844,104 | A | | 7/1989 | Martin |
| 5,076,423 | A | | 12/1991 | Russack |
| D329,137 | S | * | 9/1992 | Hinson .......................... D3/208 |
| 5,163,561 | A | | 11/1992 | Fitzgerald |
| D339,215 | S | | 9/1993 | Spencer, Jr. |
| D361,405 | S | * | 8/1995 | Tipp ................................ D28/65 |
| D364,708 | S | | 11/1995 | Tarrson et al. |
| D371,222 | S | | 6/1996 | Spencer, Jr. et al. |
| 5,566,872 | A | * | 10/1996 | Dolan et al. ..................... 225/41 |
| D381,468 | S | | 7/1997 | Dolan et al. |
| D387,493 | S | * | 12/1997 | Hester ............................. D28/67 |
| D389,053 | S | | 1/1998 | Sherman et al. |
| 5,762,079 | A | * | 6/1998 | Protonantis .................... 132/325 |
| 5,787,907 | A | | 8/1998 | Endelson |
| 5,806,666 | A | * | 9/1998 | Chiang et al. ................. 206/63.5 |
| D399,604 | S | | 10/1998 | Wolff |
| 5,836,319 | A | * | 11/1998 | Lombardi ...................... 132/287 |
| 5,931,659 | A | | 8/1999 | Wu |
| D423,721 | S | | 4/2000 | Tolentino et al. |
| 6,189,545 | B1 | * | 2/2001 | Tamez ........................... 132/321 |
| 6,227,208 | B1 | * | 5/2001 | Imbert .......................... 132/304 |
| 6,295,996 | B1 | | 10/2001 | Dickie |

(Continued)

*Primary Examiner* — Todd Manahan
*Assistant Examiner* — Vanitha Elgart
(74) *Attorney, Agent, or Firm* — Workman Nydegger (57) ABSTRACT

A compact mirror floss container configured to dispense floss includes: (i) a first clam shell member having a mirrored interior surface and (ii) a second clam shell member pivotally coupled to the first clam shell member. The second clam shell member includes a receiving mechanism. A floss cartridge is coupled about the receiving mechanism and configured to dispense floss. An attachment member is coupled to one of the first clam shell member and second clam shell member, configured to selectably couple to a receiving member. The container also includes a securing mechanism coupled to one of the first clam shell member and second clam shell member, configured to selectably couple the first clam shell member to the second clam shell member. The container also includes a cutting member configured to cut floss; and a decorative cover. The decorative cover is selectably coupleable to the clam shell members.

11 Claims, 4 Drawing Sheets

U.S. PATENT DOCUMENTS

| | | |
|---|---|---|
| 6,295,997 B1 | 10/2001 | Dickie |
| 6,484,732 B1 * | 11/2002 | Simister .................. 132/309 |
| 6,715,603 B1 | 4/2004 | Uribe |
| D491,313 S | 6/2004 | Schrott |
| 6,766,809 B2 | 7/2004 | Brattesani et al. |
| D510,461 S | 10/2005 | Vu |
| D540,676 S | 4/2007 | Novos et al. |
| D542,664 S | 5/2007 | Mayers |
| 7,213,604 B2 * | 5/2007 | Romine .................. 132/325 |
| 7,267,126 B1 | 9/2007 | Banegas |
| 2002/0020427 A1 * | 2/2002 | Lin .................. 132/325 |
| 2003/0029472 A1 * | 2/2003 | Adler .................. 132/325 |
| 2004/0173498 A1 * | 9/2004 | Lee .................. 206/581 |
| 2006/0112966 A1 * | 6/2006 | Phue .................. 132/296 |
| 2009/0308782 A1 * | 12/2009 | Grist .................. 206/581 |
| 2011/0041869 A1 * | 2/2011 | Longoni et al. .................. 132/324 |

* cited by examiner

COMPACT MIRROR FLOSS CONTAINER

BACKGROUND OF THE INVENTION

1. Field of the Invention

The present invention relates to compact containers, specifically a compact mirror floss container.

2. Description of the Related Art

The use of dental floss is highly recommended by the dental profession as a necessary adjunct to oral hygiene. Indeed, the dental profession recommends the teeth should be flossed using an appropriate dental floss, at least once daily; for example and particularly, as part of the evening ablutions prior to retiring for the night. Typically, dental floss is sold in a container that serves as the dispenser of the floss. Typically, when it is not actually being used to dispense dental floss, the container/dispenser is hidden from view such as in a drawer, a medicine cabinet, or the like. This generally results in less than diligent flossing practice.

Indeed, recent studies reveal that only about 20 percent of the population of North America flosses regularly, although it is assumed that between 70 percent and up to 90 percent of all households have at least one dental floss container in their possession. Moreover, it had been noted that there seems to be less of a tendency to want to use a dental floss dispenser which requires it to be held in one hand while dental floss is removed from the dispenser with the other hand, especially in those circumstances where the cutter for the dental floss is exposed and represents a risk to the fingers of the user. Still further it has been noted that most commercially available dental floss dispensers are awkward to use in that the spacing between the opening of the dispenser where the dental floss exits from the interior thereof to the cutter is generally quite small, so that grasping the dental floss in that region so as to remove the length of dental floss from the container is difficult. In addition, the user does not have the capability of viewing the region being flossed, when not around a restroom or mirror.

Some improvements have been made in the field. Examples of references related to the present invention are described below, and the supported teachings of each reference are incorporated by reference herein:

U.S. Pat. No. 6,715,603, issued to Uribe, discloses a dental care kit assembly having a plurality of operative components such as one or more dental floss assemblies and a cleaning implement located within separated areas or compartments of a container. The container has a substantially flat, predetermined, reduced size configuration, closely corresponding to the size of a conventional credit card thereby enabling it to be conveniently carried on the person of a user. The reduced size container and the various components contained therein may be structured to be disposable after a single or a limited number of uses or alternatively may be of a more permanent structure capable of being used over a more extended period of time.

U.S. Pat. No. 5,163,561, issued to Fitzgerald, discloses a dental cleaning kit that includes a housing arranged with a cavity directed therethrough, with a trough positioned in communication with the cavity at a lower distal end of the front wall and floor of the housing to accommodate a plurality of replaceable toothbrush heads thereon. A side wall of the housing includes a handle structure to receive in a selective manner cleaning components to include a toothpick head and a dental floss holder head. A modification of the invention includes a mirror handle and mirror mounted to the side wall within a loop structure, as well as a further mirror member mounted to a deformable goose neck conduit secured to the first side wall to permit ease of visual observation by an individual during use of the apparatus.

U.S. Pat. No. 6,766,809, issued to Brattesani et al., discloses a floss dispenser comprising a body configured for holding and dispensing floss and a gripping arm extending from the body configured to facilitate gripping by the user while floss is dispensed and cut from the dispenser. The body houses a spool of floss and includes a hole for dispensing the floss and a hole for connecting the floss dispenser to a key ring or chain. A floss cutter is included in the body or the gripping arm. In one embodiment the gripping arm comprises an operational key. The gripping arm is either integrally or removably connected with the body. In one embodiment, the body comprises a clam shell case configured to hold the head of a key. In another embodiment, the body comprises a sheath type pocket configured to hold the head of a key. The floss dispensers may also comprise other features, including lights and a toothpick.

U.S. Pat. No. 5,076,423, issued to Russack, discloses a dental floss dispenser that has a wallet sized case with a pair of faces and an aperture dispensing edge. A spool rotatably mounted in the case has a floss winding volume with a radial dimension many times greater than its axial dimension. Floss is spirally wound about the spool. A cutter is mounted on the outside of said case for catching and cutting the floss at the same location.

U.S. Pat. No. 6,295,996, issued to Dickie, discloses a dispenser for dental floss comprising a closed container having a reel of dental floss disposed therein, and having a generally planar back face, a front face, a pair of opposed side faces, a top face, a bottom face opposed to the top face, and a corner at each intersection of the top and bottom faces with the pair of opposed side faces. A hub is centrally located in the interior of the closed container and extends between the interior surfaces of the front and back faces. The reel of dental floss is mounted for rotation about the hub. There is an opening in the front face at a first corner, through which a strand of dental floss extends so as to be unwound from the reel; and a friction and cutting member is at a second corner of the front face. The friction and cutting member comprises a tongue portion which is angled away from a base portion, and is secured in place at the second corner of the front face. The front face is concave on an axis extending between a pair of diagonally opposed corners of the container, the concavity being defined by ridges formed in the front face at the first corner, and at a diagonally opposed corner. A C-shaped chute is formed at the second corner, and is positioned such that the dental floss extends from the opening at the first corner through the C-shaped chute located at the second corner.

U.S. Pat. No. 6,295,997, issued to Dickie, discloses a dispenser for dental floss comprising a closed container having a reel of dental floss disposed therein, and having a generally planar back and front face, a pair of opposed side faces, a bottom face, and a top face opposed to the bottom face. There is a hub centrally located in the interior of the closed container, the reel of dental floss is mounted for rotation about the hub when the dental floss is unwound and removed from the reel. A slot is formed in the top face near a first corner of the container, through which slot a strand of dental floss extends so as to be unwound from the reel. A channel is formed at a second corner of the container, at the intersection of the top face and a second side face, and the channel extends between the top face and the second side face. A friction and cutting member comprises a tongue portion which is angled away from a base portion thereof, and is secured in place within the channel. The top face is concave on a centrally located axis extending between the back face and the front face, the concavity being defined by ridges located at the first and second corners. Thus the slot is located in the first ridge at the first corner, and the channel extends through the second ridge at the second corner.

U.S. Pat. No. 4,254,786, issued to Won, discloses a dental floss holder with a slot-headed locking axle on which a spool of floss is mounted. A length of floss is extracted from the spool disposed within the holder and is spanned across two spaced prongs formed on the holder and locked to the axle by being wound about one side of the slotted head before spanning and the other side of the slotted head after spanning. Tension is applied to the spanned floss by rotating the locking axle which is held in position by a ratcheting spring clip to provide a taut span of floss which can be manipulated between the user's teeth.

U.S. Design Pat. No. D491,313, issued to Schrott, discloses an ornamental design for a dental floss holder in credit card form.

The inventions heretofore known suffer from a number of disadvantages which include being limited in application, being limited in versatility, being cumbersome, being difficult to use, being expensive, and being limited in adaptability.

What is needed is a compact mirror floss container that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available floss containers. Accordingly, the present invention has been developed to provide an efficient and effective device to floss your teeth.

A compact mirror floss container configured to dispense floss may be comprised of a first clam shell member, wherein the first clam shell member may have a mirrored interior surface. The mirrored interior surface may also be convexed. A second clam shell member may be pivotly coupled to the first clam shell member, wherein the second clam shell member includes a receiving mechanism. The receiving mechanism may be disposed on an interior surface of the second clam shell member. A floss cartridge may be coupled about the receiving mechanism, wherein the floss cartridge may be configured to dispense floss. The container may also include an attachment member, wherein the attachment member may be coupled to one of the first clam shell member and second clam shell member. The attachment member may be configured to selectably couple to a receiving member. The container may further include a securing mechanism, wherein the securing mechanism may be coupled to one of the first clam shell member and second clam shell member. The securing mechanism may be configured to selectably couple the first clam shell member to the second clam shell member.

The floss cartridge may include a center section, wherein the center section may be configured to secure and rotate about the receiving mechanism. The floss cartridge may also be removably coupleable to the receiving mechanism. The receiving mechanism may include a rotatable axis, wherein the floss cartridge may rotate about the rotatable axis. The receiving mechanism may also include a post, wherein the floss cartridge may rotate about the post. The floss cartridge may be permanently coupled to the second clam shell member.

The second clam shell member may also include a support member, wherein the support member may be configured to support and secure an end of the floss. The first clam shell member and the second clam shell member may further comprise a decorative cover, wherein the decorative cover may be removably coupleable from the first and second calm shell members. The first clam shell member and the second clam shell member may be frictionally and pivotly coupled, wherein the first and second shell members may be configured to secure at about 60 to 180 degrees relative to one another. The first clam shell member and second clam shell member may further comprise a cutting member, wherein the cutting member may be configured to cut floss from the floss cartridge.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not therefore to be considered to be limiting of its scope, the invention will be described and explained with additional specificity and detail through the use of the accompanying drawing(s), in which.

DETAILED DESCRIPTION OF THE INVENTION

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment or example is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is, are," "characterized by," and grammatical equivalents thereof are inclusive or open-ended terms that do not exclude additional unrecited elements or method steps. "Comprising" is to be interpreted as including the more restrictive terms "consisting of" and "consisting essentially of."

Figure 1:
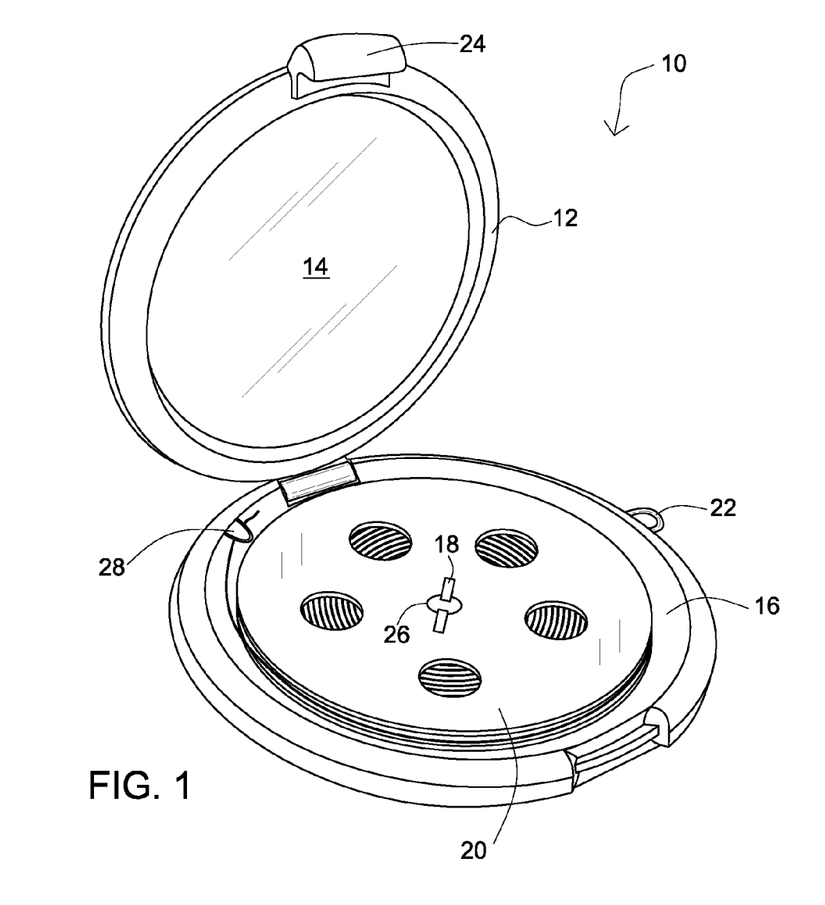
FIG. 1 is a top perspective view of a compact mirror floss container, according to one embodiment of the invention.

FIG. 1 illustrates a compact mirror floss container 10 configured to dispense floss, comprising a first clam shell member 12 having a mirrored interior surface 14. One non limiting example of a mirrored interior surface 14 is a mirror having a transparent layer based on an opaque layer. The container 10 also includes a second clam shell member 16 pivotly coupled to the first clam shell member 12. The first clam shell member 12 and the second clam shell member 16 are frictionally pivotly coupled together, wherein the first and second shell members 12, 16 may be configured to secure at about 60 to 180 degrees relative to one another. Accordingly, the second clam shell member 16 includes a receiving mechanism 18 on an interior surface of the second clam shell member 16. The receiving mechanism 18 is configured to secure and receive a floss cartridge 20, wherein the floss cartridge 20 is configured to store and dispense floss.

The container further includes an attachment member 22 coupled to one of the first clam shell member 12 and second clam shell member 16, configured to provide an anchor point for selectable attachment, thereto. The illustrated attachment member 22 is a loop, configured to provide a support for a receiving member. One non-limiting example of a receiving member is a keychain. In addition, a securing mechanism 24 is coupled to one of the first clam shell member 12 and second clam shell member 16, wherein the securing mechanism 24 is configured to selectably couple the first clam shell member 12 to the second clam shell member 16. The illustrated securing mechanism 24 is configured to restrict the pivotal motion of the first and second clam shell members 12, 16. One non-limiting example of a securing mechanism 24 is a clasp and lock, configured on one of the first and second clam shell members 12, 16.

The illustrated floss cartridge 20 includes a center section 26 configured to secure and rotate about the receiving mechanism 18, wherein the floss cartridge 20 is removably coupleable to the receiving mechanism 18. The receiving mechanism 18 includes a rotatable axis, wherein the floss cartridge rotates about the axis when dispensing floss. The rotatable axis of the receiving mechanism may include a post, wherein the floss cartridge rotates about the post when dispensing floss.

The container 10 also includes a cutting member 28, disposed on one of the first and second clam shell members 12, 16, wherein the cutting member 28 is configured to cut floss from the floss cartridge 20. The cutting member 28 is configured about the floss cartridge 20, wherein advantageously the cutter is visible in the mirrored interior surface 14 during use.

Figure 2:
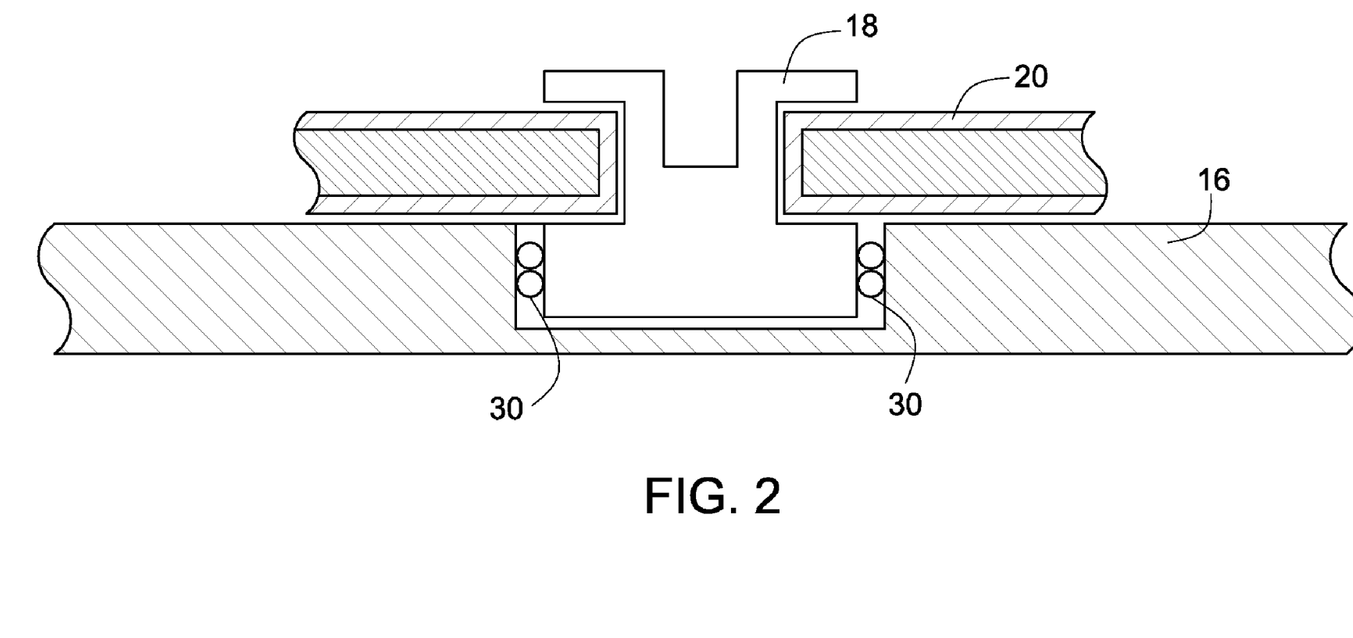
FIG. 2 is a side cross sectional view of a receiving mechanism of a compact mirror floss container, according to one embodiment of the invention.

FIG. 2 illustrates a cross sectional side view of a second clam shell member 16 including a receiving mechanism 18, wherein the receiving mechanism 18 is coupled to a floss cartridge 20. In one embodiment of the receiving mechanism 18, the receiving mechanism includes a rotatable axis, wherein the axis includes a plurality of rotating members 30. One non-limiting example of a rotating member 30 is a ball bearing. The rotating members 30 enable the rotatable axis of the receiving mechanism 18 to rotate about the interior surface of the second clam shell member 16. The floss cartridge 20 is secured to the receiving mechanism 18 and thereby rotates about the interior surface of the second calm shell member 16. The rotation of the floss cartridge 20 enables the dispensing of floss.

Figure 3:
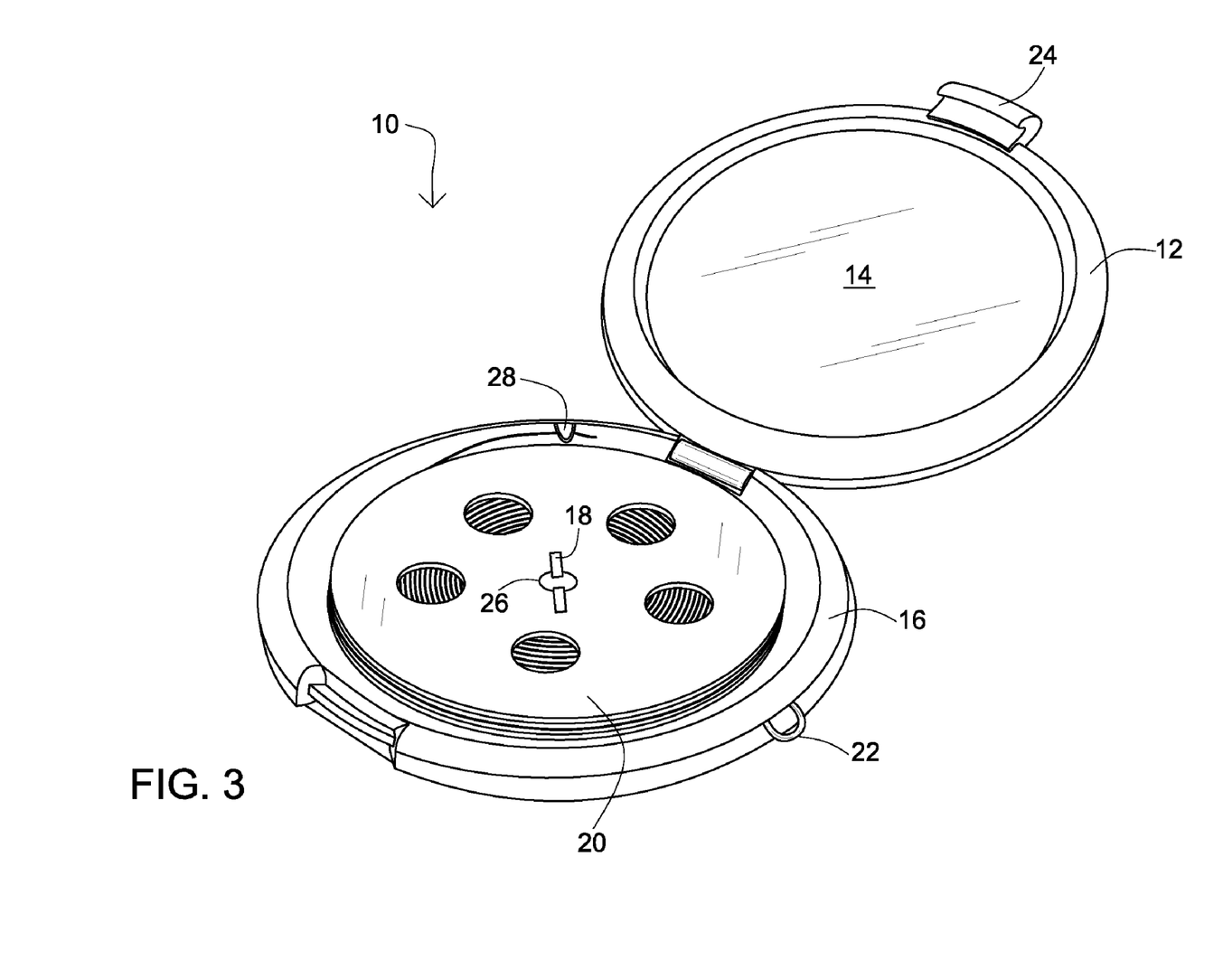
FIG. 3 is a top plan view of a compact mirror floss container, according to one embodiment of the invention.

FIG. 3 illustrates a compact mirror floss container 10 comprising of a first clam shell member 12, having a mirrored interior surface 14, and a second clam shell 16 member, wherein the first and second clam shell members 12, 16 are frictionally pivotly coupled together. The container may be configured to secure at about 180 degrees relative to one another. The container also includes a receiving mechanism 18, an attachment member 22, a securing mechanism 24, a cutting member 28, a floss cartridge 20, disposed on one of the first and second clam shell members 12, 16. The floss cartridge 20 also includes a center section 26.

Figure 4:
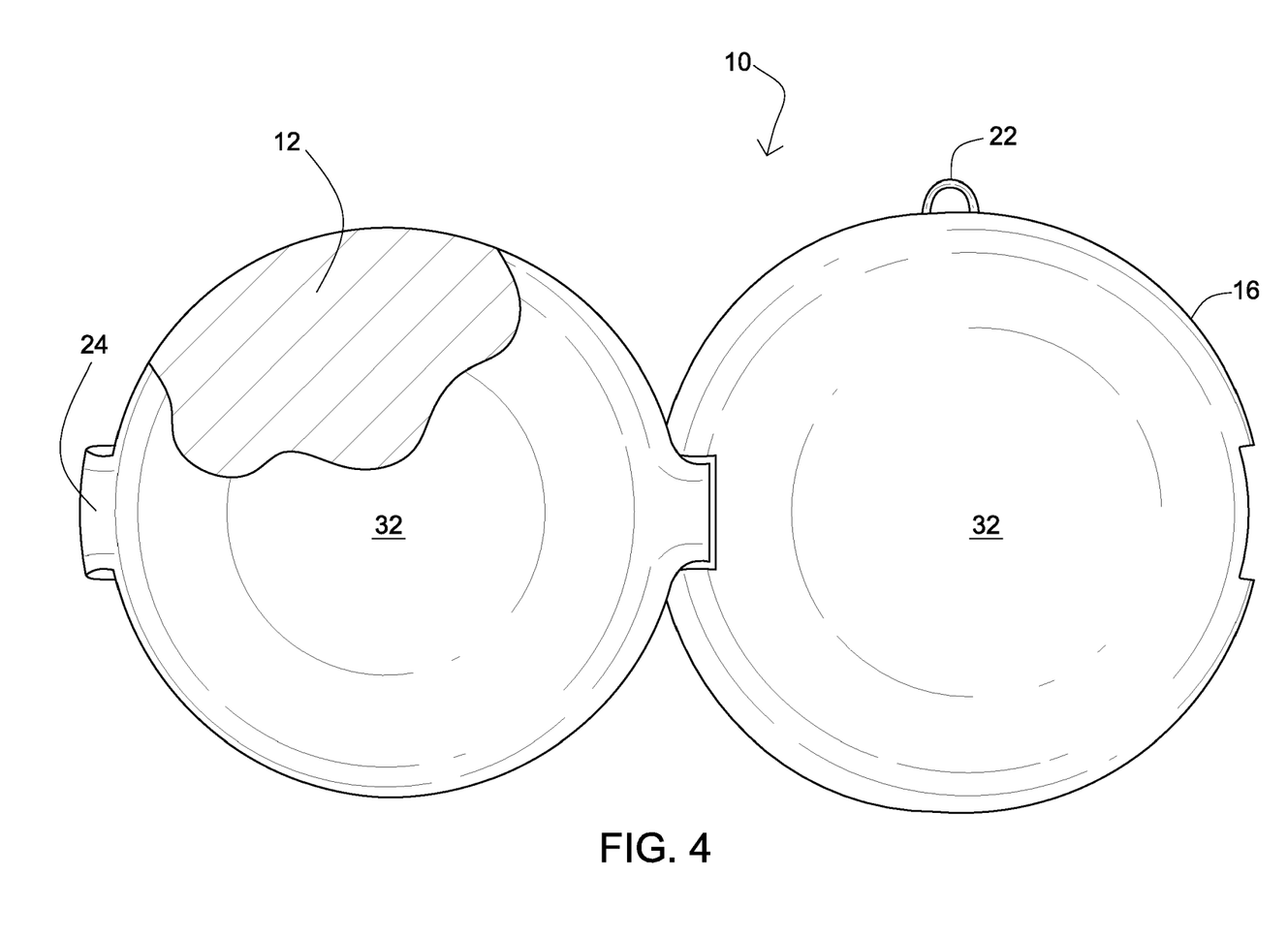
FIG. 4 is bottom plan view of a compact mirror floss container, according to one embodiment of the invention.

FIG. 4 illustrates a compact mirror floss container 10 comprising of a first clam shell member 12 and a second clam shell member 16 pivotly coupled together. The container 10 also includes a decorative cover 32, wherein the decorative cover 32 protects the exterior surface of the first and second clam shell members 12, 16. In addition, the decorative cover 32 may be removably coupleable to the first and second clam shell members 12, 16. In addition, the container further includes a securing mechanism 24 and an attachment member 22.

In operation of one embodiment of the container 10, a user uncouples the securing mechanism 24 of the first and second clam shell members 12, 16; thereby opening the container 10 for use. The user may engage an end of the floss from the floss cartridge 20 and pull the floss, thereby unraveling the floss from the floss cartridge 20. The user may cut the floss from the floss cartridge 20 by the cutting member 28. The user configures the mirrored interior surface 14 of the first clam shell member 12 to view the teeth when the user is flossing. The floss cartridge 20 may be replaced by uncoupling the center section 26 of the floss cartridge 20 from the receiving mechanism 18. The floss cartridges may be in disposable form.

In operation of another embodiment of the invention, a user may couple the attachment member 22 of the container 10 to a keychain, purse zipper, or any other convenient location. In addition, the user may interchange the decorative cover 32 of the container to a particular design, color, and configuration.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

It is envisioned that the first and second clam shell members may include a variety of shapes, designs, configurations, and still perform the intended function. Examples are described in, but not limited to the following U.S. Pat. Nos. D271,431; D542,664; D540,676; D423,721; D399,604; D510,461; 5,806,666; D389,053; D381,468; D371,222; D364,708; D339,215.

For example, although the figures illustrate a receiving mechanism, one skilled in the art would appreciate that the receiving mechanism may be but not limited to a post, a rotatable axis, a pin, etc., and still perform its intended function.

Additionally, although the figures illustrate an attachment member, one skilled in the art would appreciate that the attachment member may be but not limited to: a hook, a magnet, a clasp, a ring, a loop, etc., and still performs its intended function.

Furthermore, although the figures illustrate a decorative cover, one skilled in the art would appreciate that the decorative cover may vary in size, shape, configuration, design, color, length, width, depth, height, and still perform its intended function.

It is also envisioned that, one skilled in the art would appreciate that the mirrored interior surface may be convexed or concaved in configuration; and still perform its intended function.

It is expected that there could be numerous variations of the design of this invention. An example is that, one skilled in the art would appreciate that the container may vary in size, shape, configuration, design, color, length, width, depth, height, and still perform its intended function.

Finally, it is envisioned that the components of the device such as the first clam shell member, the second clam shell member, the receiving mechanism, the attachment member, the securing member, the floss cartridge, the mirrored interior surface, and the decorative cover may be constructed of a variety of materials, such as but not limited to: metal, metal alloys, plastic, plastic composites, rubber, rubber composites, glass, and still perform its intended function.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. A compact configured to dispense floss, comprising:
   a) a first clam shell member having a mirrored interior surface;
   b) a second clam shell member pivotally coupled to the first clam shell member, including:
      b1) a receiving mechanism, positioned and rotatively coupled centrally to an interior surface of the second clam shell member; and
      b2) a floss cartridge coupled about the receiving mechanism, the floss cartridge having:
         i) a circular spool that has a periphery that extends adjacent and equidistant to the interior perimeter surface of the second clam shell and sized to substantially fill an interior of the second clam shell so as to nearly abut the interior perimeter surface; and
         ii) a length of floss wrapped about the circular spool of the floss cartridge; and
      b3) a cutting member, coupled to the interior perimeter surface of the second clam shell to removably retain an end of the floss within the second clam shell when the floss is completely stored within the compact, and configured to cut the floss when a portion of the floss is withdrawn from the floss cartridge to be used by a user; and
   c) a securing mechanism configured to selectably couple the first clam shell member to the second clam shell member, thereby restricting the pivotal motion of the first and second clam shell members.

2. The compact of claim 1, wherein the floss cartridge includes a center section configured to secure and rotate about the receiving mechanism.

3. The compact of claim 1, wherein the floss cartridge is removably coupleable to the receiving mechanism.

4. The compact of claim 1, wherein the receiving mechanism includes a rotatable axis.

5. The compact of claim 1, wherein the receiving mechanism includes a post.

6. The compact of claim 1, wherein the mirrored interior surface is a convexed surface.

7. The compact of claim 1, wherein the floss cartridge is permanently coupled to the second clam shell member.

8. The compact of claim 1, wherein each of the first clam shell member and the second clam shell member further comprises a decorative cover.

9. The compact of claim 8, wherein each of the decorative covers is removably coupleable.

10. The compact of claim 1, wherein the first clam shell member and the second clam shell member are frictionally pivotally coupled, wherein the first and second shell members may be configured to secure at about 60 to 180 degrees relative to one another.

11. A compact configured to dispense floss, comprising:
   a) a first clam shell member having a mirrored interior surface;
   b) a second clam shell member pivotally coupled to the first clam shell member, including:
      b1) a receiving mechanism, positioned and rotatively coupled centrally to an interior surface of the second clam shell member; and
      b2) a floss cartridge coupled about the receiving mechanism, the floss cartridge having:
         i) a circular spool that has a periphery that extends adjacent and equidistant to the interior perimeter surface of the second clam shell and sized to substantially fill an interior of the second clam shell so as to nearly abut the interior perimeter surface; and ii) a length of floss wrapped about the circular spool of the floss cartridge; and b3) a cutting member, coupled to the interior perimeter surface of the second clam shell, configured to removably retain an end of the floss within the second clam shell when the floss is completely stored within the compact, and configured to cut the floss when a portion of the floss is withdrawn from the floss cartridge to be used by a user;

c) a securing mechanism configured to selectably couple the first clam shell member to the second clam shell member, thereby restricting the pivotal motion of the first and second clam shell members;

wherein the floss cartridge includes a center section configured to secure and rotate about the receiving mechanism;

wherein the floss cartridge is removably coupleable to the receiving mechanism wherein the receiving mechanism includes a rotatable axis;

wherein the rotatable axis includes a post;

wherein the mirrored interior surface is a convex surface;

wherein each of the first clam shell member and the second clam shell member further comprises a decorative cover;

wherein the decorative cover is removably coupleable; and wherein the first clam shell member and the second clam shell member are frictionally and pivotally coupled, wherein the first and second shell members may be configured to secure at about 60 to 180 degrees relative to one another.

* * * * *

UNITED STATES PATENT AND TRADEMARK OFFICE
CERTIFICATE OF CORRECTION

PATENT NO. : 8,272,389 B2
APPLICATION NO. : 12/027569
DATED : September 25, 2012
INVENTOR(S) : Bish It is certified that error appears in the above-identified patent and that said Letters Patent is hereby corrected as shown below:

In the Specifications:

Column 2
Line 38, change "reel; and a friction" to --reel, and a friction--

Column 3
Line 42, change "pivotly" to --pivotally--

Column 4
Line 8, change "pivotly" to --pivotally--
Line 47, change "schematics representations" to --schematic representations--

Column 5
Line 42, change "non limiting" to --non-limiting--
Line 45, change "pivotly" to --pivotally--
Line 48, change "pivotly" to --pivotally--

Column 6
Line 39, change "pivotly" to --pivotally--
Line 48, change "pivotly" to --pivotally--
Line 62, change "floss cartridge 20 by" to --floss cartridge 20 with--

Column 7
Line 23, change "D364,708; D339,215." to --D364,708; and D339,215.--
Line 41, change "configuration; and" to --configuration, and--
Line 53, change "such as but not limited to:" to --such as, but not limited to,:--

Signed and Sealed this
Twenty-eighth Day of May, 2013

Teresa Stanek Rea
*Acting Director of the United States Patent and Trademark Office*